(12) United States Patent
Bessette et al.

(10) Patent No.: US 12,406,076 B2
(45) Date of Patent: Sep. 2, 2025

(54) ELECTRONIC RECORDS SYSTEM AND RELATED METHODS

(71) Applicant: Luc Bessette, Montreal (CA)

(72) Inventors: Luc Bessette, Montreal (CA); Yves Leborgne, Montreal (CA)

(73) Assignee: LUC BESSETTE, Montreal (CA)

( * ) Notice: Subject to any disclaimer, the term of this patent is extended or adjusted under 35 U.S.C. 154(b) by 96 days.

(21) Appl. No.: 18/574,695

(22) PCT Filed: Jul. 4, 2022

(86) PCT No.: PCT/CA2022/051055
§ 371 (c)(1),
(2) Date: Dec. 27, 2023

(87) PCT Pub. No.: WO2023/279200
PCT Pub. Date: Jan. 12, 2023

(65) Prior Publication Data
US 2024/0296237 A1 Sep. 5, 2024

Related U.S. Application Data

(60) Provisional application No. 63/218,022, filed on Jul. 2, 2021.

(51) Int. Cl.
*G06F 21/00* (2013.01)
*G06F 21/31* (2013.01)
*G06F 21/60* (2013.01)

(52) U.S. Cl.
CPC ............ *G06F 21/606* (2013.01); *G06F 21/31* (2013.01)

(58) Field of Classification Search
CPC ...... G06F 21/606; G06F 21/31; G06F 16/901; G06F 21/6245; G06F 16/93;
(Continued)

(56) References Cited

U.S. PATENT DOCUMENTS 7,578,432 B2   8/2009   Libin et al.
7,971,059 B2   6/2011   Caiman
(Continued)

FOREIGN PATENT DOCUMENTS

CA   2239015        12/2005
EP   3422221 A1    1/2019
(Continued)

OTHER PUBLICATIONS

International Search Report issued Jul. 27, 2016 in connection with International PCT Patent Application PCT/CA2016/050424, 4 pages.
(Continued)

*Primary Examiner* — Kendall Dolly

(57) ABSTRACT

A system for secure communication of personal information, including a server arrangement in communication with one or more databases storing personal information associated with multiple users. The system includes a machine-readable storage encoded with non-transitory program code executable by one or more processors of a mobile communication device of a user to implement on the mobile communication device a user application to manage retrieval of personal information stored in the one or more databases. The user application including a user interface manager to manage a Graphical User Interface (GUI) to manage display of information to the user and manage user inputs through the GUI, and a data exchange control manager to manage exchange of data between the mobile device and the server arrangement. The mobile communication device is configured to communicate with the server arrangement by establishing and monitoring a stateless communication session including an encrypted communication channel.

23 Claims, 9 Drawing Sheets

(58) Field of Classification Search
CPC .... G06Q 2220/00; G06Q 10/10; G06Q 40/00; G06Q 50/22; G06Q 50/26; G06Q 50/18; H04W 12/033; H04W 12/06; G16H 10/60; H04L 63/102

See application file for complete search history.

(56) References Cited

U.S. PATENT DOCUMENTS

| | | | |
|---|---|---|---|
| 7,974,924 | B2 | 7/2011 | Holla et al. |
| 8,090,590 | B2 | 1/2012 | Fotsch et al. |
| 9,195,797 | B2 | 11/2015 | Bessette |
| 10,366,204 | B2* | 7/2019 | Tanner, Jr. ............. G06Q 40/08 |
| 10,404,464 | B2* | 9/2019 | Kamal .................. H04L 9/3231 |
| 11,862,306 | B1* | 1/2024 | Goldberg ............. H04L 9/0637 |
| 2004/0117215 | A1 | 6/2004 | Marchosky |
| 2005/0075543 | A1 | 4/2005 | Calabrese |
| 2006/0129434 | A1 | 6/2006 | Smitherman et al. |
| 2007/0198436 | A1 | 8/2007 | Weiss |
| 2008/0021834 | A1 | 1/2008 | Holla et al. |
| 2008/0027752 | A1 | 1/2008 | Phan et al. |
| 2008/0040151 | A1 | 2/2008 | Moore |
| 2008/0306872 | A1 | 12/2008 | Felsher |
| 2010/0063843 | A1 | 3/2010 | Kenedy et al. |
| 2011/0246231 | A1 | 10/2011 | Sie |
| 2012/0203571 | A1 | 8/2012 | Crapo et al. |
| 2012/0203798 | A1 | 8/2012 | Gifford et al. |
| 2012/0265702 | A1 | 10/2012 | Maher |
| 2013/0179195 | A1* | 7/2013 | Lorsch .................. G16H 40/67 705/3 |
| 2013/0208955 | A1 | 8/2013 | Tiecheng |
| 2013/0346103 | A1 | 12/2013 | Griffin et al. |
| 2014/0058751 | A1 | 2/2014 | Eaves et al. |
| 2014/0089001 | A1 | 3/2014 | Macoviak et al. |
| 2014/0156299 | A1 | 6/2014 | Malven et al. |
| 2014/0164022 | A1 | 6/2014 | Reed et al. |
| 2014/0164784 | A1 | 6/2014 | Sinderbrand |
| 2014/0244296 | A1 | 8/2014 | Linn et al. |
| 2014/0257850 | A1 | 9/2014 | Walker et al. |
| 2014/0289001 | A1 | 9/2014 | Shelton |
| 2014/0324473 | A1 | 10/2014 | Bormann et al. |
| 2014/0358574 | A1 | 12/2014 | Tara |
| 2015/0066538 | A1 | 3/2015 | Dantsker et al. |
| 2015/0244687 | A1 | 8/2015 | Perez et al. |
| 2017/0068785 | A1 | 3/2017 | Experton et al. |
| 2018/0082020 | A1 | 3/2018 | Rajagopal et al. |
| 2018/0146374 | A1 | 5/2018 | Golan et al. |
| 2018/0173883 | A1* | 6/2018 | Gandhi ................. G06F 21/604 |
| 2019/0027237 | A1* | 1/2019 | McFarlane ............. G16H 80/00 |
| 2019/0043281 | A1 | 2/2019 | Aman |
| 2019/0356479 | A1* | 11/2019 | Grimme ................ H04L 9/0825 |
| 2020/0005912 | A1* | 1/2020 | Saliman ................. G16H 20/00 |
| 2020/0034850 | A1 | 1/2020 | Weiss |
| 2021/0319116 | A1* | 10/2021 | Jarvis ..................... G16H 10/60 |
| 2022/0052847 | A1* | 2/2022 | Gonzalez Cervantes ................... G06F 21/6245 |
| 2023/0129639 | A1 | 4/2023 | Bessette et al. |
| 2023/0385450 | A1 | 11/2023 | Bessette et al. |
| 2023/0402140 | A1 | 12/2023 | Bessette et al. |

FOREIGN PATENT DOCUMENTS

| | | |
|---|---|---|
| WO | 2003019901 A1 | 3/2003 |
| WO | 2014085775 A1 | 6/2014 |
| WO | 20140105752 A1 | 7/2014 |
| WO | 2018152410 A1 | 8/2018 |
| WO | 2023279200 | 1/2023 |

OTHER PUBLICATIONS

Written Opinion issued Jul. 27, 2016 in connection with International PCT Patent Application PCT/CA2016/050424, 5 pages.
Restriction Requirement issued on Sep. 17, 2019, in connection with U.S. Appl. No. 15/568,217, 6 pages.
Non-Final Office Action issued on Mar. 31, 2020 in connection with U.S. Appl. No. 15/568,217, 11 pages.
Final Office Action issued Jan. 19, 2021 in connection with U.S. Appl. No. 15/568,217, 23 pages.
Examiner's Report issued May 21, 2021 in connection with Canadian Patent Application No. 2983466, 5 pages.
Examiner's Report issued Sep. 14, 2021 in connection with Canadian Patent Application No. 2983466, 5 pages.
Examiner's Report issued on May 28, 2024 in connection with Canadian Patent Application No. 2983466, 15 pages.
Examiner's Report issued Nov. 1, 2021 in connection with Canadian Patent Application No. 2983466, 5 pages.
Examiner's Report issued Dec. 17, 2021 in connection with Canadian Patent Application No. 2983466, 4 pages.
Examiner's Report issued on Jun. 17, 2022, in connection with Canadian Patent Application No. 2983466, 5 pages.
Examiner's Report issued on Mar. 23, 2023, in connection with Canadian Patent Application No. 2983466, 4 pages.
Examiner's Report issued on May 30, 2023, in connection with Canadian Patent Application No. 2983466, 8 pages.
Examiner's Report issued on Nov. 28, 2023, in connection with Canadian Patent Application No. 2983466, 10 pages.
Examiner's Report issued on Dec. 23, 2022, in connection with Canadian Patent Application No. 2983466, 7 pages.
Non-Final Office Action issued Sep. 1, 2021, in connection with U.S. Appl. No. 17/379,358, 30 pages.
Non-Final Office Action issued on Feb. 9, 2023, in connection with U.S. Appl. No. 17/379,358, 36 pages.
Final Office Action issued on Dec. 15, 2021, in connection with U.S. Appl. No. 17/379,358, 25 pages.
Examiner's Report issued Dec. 7, 2021, in connection with Canadian Patent Application No. 3136291, 4 pages.
Examiner's Report issued on Dec. 28, 2022, in connection with Canadian Patent Application No. 3136291, 5 pages.
Examiner's Report issued on Jun. 20, 2022, in connection with Canadian Patent Application No. 3136291, 6 pages.
Examiner's Report issued Dec. 8, 2021, in connection with Canadian Patent Application No. 3136300, 4 pages.
Examiner's Report issued Apr. 17, 2023, in connection with Canadian Patent Applicaiton No. 3136300, 12 pages.
Examiner's Report issued on Jun. 10, 2022, in connection with Canadian Patent Application No. 3136300, 10 pages.
Examiner's Report issued on Feb. 6, 2023, in connection with Canadian Patent Application No. 3136300, 7 pages.
Examiner's Report issued on Jun. 27, 2023, in connection with Canadian Patent Application No. 3136300, 8 pages.
Examiner's Report issued on Dec. 14, 2023, in connection with Canadian Patent Application No. 3136300, 10 pages.
Examiner's Report issued on May 31, 2024, in connection with Canadian Patent Application No. 3136300, 14 pages.
Examiner's Report issued on Dec. 16, 2022, in connection with Canadian Patent Application No. 3136300, 5 pages.
Examiner's Report issued Dec. 31, 2021, in connection with Canadian Patent Application No. 3137320, 10 pages.
Examiner's Report issued on May 26, 2023, in connection with Canadian Patent Application No. 3137320, 10 pages.
Examiner's Report issued on Jun. 22, 2022, in connection with Canadian Patent Application No. 3137320, 11 pages.
Examiner's Report issued on Mar. 23, 2023, in connection with Canadian Patent Application No. 3137320, 5 pages.
Examiner's Report issued on Nov. 8, 2022, in connection with Canadian Patent Application No. 3137320, 10 pages.
Wilson et al., "Travel vaccines enter the digital age: Creating a virtual immunization record", American Journal of Tropical Medicine and Hygiene, 94(3), pp. 485-488, URL (accessed May 24, 2023): https://www.ncbi.nlm.nih.gov/pmc/articles/PMC4775877/, published Mar. 2016 (Mar. 2016).
International Search Report and Written Opinion issued on Sep. 29, 2022, in connection with International PCT Patent Application No. PCT/CA2022/051055, 11 pages.
Examiner's Report issued on Mar. 22, 2024, in connection with Canadian Patent Application No. 3108555, 7 pages.

(56) References Cited

OTHER PUBLICATIONS

Examiner's Report issued on Mar. 22, 2024, in connection with Canadian Patent Application No. 3081531, 5 pages.
Examiner's Report issued on Mar. 22, 2024, in connection with Canadian Patent Application No. 3098242, 5 pages.
Examiner's Report issued on Apr. 15, 2024, in connection with Canadian Patent Application No. 3119570, 8 pages.
Non-Final Office Action issued on Jun. 14, 2024, in connection with U.S. Appl. No. 18/086,863, 32 pages.
Non-Final Office Action issued on Jun. 14, 2024, in connection with U.S. Appl. No. 18/236,429, 29 pages.
Examiner Report issued on Sep. 19, 2024 in connection with Canadian Patent Application No. 3197581, 8 pages.
Examiner Report issued on Nov. 13, 2024 in connection with Canadian Patent Application No. 3210039, 7 pages.
European Search Report issued on Feb. 5, 2025, in connection with European Patent Application No. 22836431.1, 10 pages.
Examiner Report issued on Mar. 10, 2025 in connection with Canadian Patent Application No. 3136300, 14 pages.
Final Office Action issued on Feb. 6, 2025, in connection with U.S. Appl. No. 18/086,863, 22 pages.
Final Office Action issued on Mar. 7, 2025, in connection with U.S. Appl. No. 18/236,429, 21 pages.
Restriction Requirement issued on Feb. 28, 2025, in connection with U.S. Appl. No. 17/994,128, 6 pages.
Restriction Requirement issued on Mar. 4, 2025, in connection with Canadian Patent Application No. 3119570, 3 pages.

\* cited by examiner

ELECTRONIC RECORDS SYSTEM AND RELATED METHODS

FIELD OF THE INVENTION

The invention generally relates to electronic records systems and related methods and in particular to secure user authentication and data access functionalities allowing a user to securely access confidential information and optionally share confidential information fully or in part with a third party.

BACKGROUND

Electronic records systems often contain confidential user information, such as medical information, financial information, technical information, commercial information, or legal information. Accordingly, data safety is a major concern during the operation of such electronic records systems. However, current electronic records systems rely on authentication mechanisms that are not secure enough, such as password-based authentication mechanisms, hence they are prone to loss of confidential data should a password become compromised. In addition, current electronic records systems do not provide a user friendly and a secure mechanism to share confidential information with a third party, in a way which is fully under control of the user, such that the user can precisely determine what information a third party is allowed to see and what information the third party is not allowed to see. Finally, the manner in which user data is stored in the data repository of the electronic record system is such that a breach or exposure over a small portion of the data can enable an intruder to access much larger quantities of confidential data.

In light of the above, there is a need in the industry for providing an improved electronic records system and related methods which alleviate, at least in part, the deficiencies with existing electronic records systems.

SUMMARY OF THE INVENTION

As embodied and broadly described herein, the invention provides a system for secure communication of personal information, comprising a server arrangement in communication with one or more databases storing personal information associated with multiple users, in respective user records, wherein the personal information is organized in each user records as a series of documents, the server arrangement including a non-transitory storage medium storing program code executable by one or more processors to implement:
 a. a user identification manager,
 b. a user profile manager,
 c. a user data access manager.

The system further includes a machine-readable storage encoded with non-transitory program code executable by one or more processors of a mobile communication device of a user to implement on the mobile device a user application to manage retrieval of personal information of the user stored in the one or more databases, the user application including:
 i. a user interface manager to manage a Graphical User Interface (GUI) to manage display of information to the user and manage user inputs through the GUI,
 ii. a user authentication manager to manage user authentication and grant access to the user application when the user is successfully authenticated,
 iii. a data exchange control manager to manage exchange of data between the mobile device and the server arrangement.

The mobile communication device is configured to communicate with the server arrangement, whereby:
 i. the user identification manager is responsive to credentials transmitted by the user application to identify a user profile associated with the user,
 ii. the user profile manager configured to generate a document index associated with the user profile, the document index identifying documents stored in the user record of the user, and transmit the document index to the user application,
 iii. the user interface manager being responsive to the document index to display via the GUI user-selectable input elements corresponding to respective documents in the user record, allowing the user to select via the GUI a document to be retrieved,
 iv. the user application configured to transmit to the user data access manager a user selection indicative of a document selected by the user to be retrieved,
 v. the user data access manager and the data exchange control manager configured to establish a stateless communication session including an encrypted communication channel and further configured to monitor transmission of the document selected by the user to be retrieved and when retrieval of the document by the mobile communication device is completed, disable the encrypted communication channel.

As embodied and broadly described herein, the invention also provides a machine-readable storage encoded with non-transitory program code executable by one or more processors of a mobile communication device of a user to implement on the mobile communication device a user application to manage retrieval of personal information of the user stored in the one or more databases associated with a server arrangement, the user application including:
 a. a user authentication manager to manage user authentication and grant access to the user application when the user is successfully authenticated, in response to successful user-authentication initiate transmission of credentials to the server arrangement allowing the server arrangement to identify a user profile at the server arrangement associated with the user,
 b. a user interface manager to manage a Graphical User Interface (GUI) to manage display of information to the user and manage user inputs through the GUI, the user interface manager being responsive to a document index transmitted from the server arrangement to display on the GUI user-selectable input elements corresponding to respective documents in a user record associated with the user profile, allowing the user to select via the GUI a document to be retrieved from the user record,
 c. a data exchange control manager configured to establish with the server arrangement a stateless communication session including an encrypted communication channel and further configured to monitor transmission of a document from the user record and corresponding to a user-selection at the GUI, via the encrypted channel, to detect a state of completion of the document transmission and in response to detection of the state of completion, disable the encrypted communication channel.

As embodied and broadly described herein the invention further provides a method for secure communication of personal information, comprising providing a server arrangement in communication with one or more databases storing personal information associated with multiple users, in respective user records, wherein the personal information is organized in each user records as a series of documents, the server arrangement including a non-transitory storage medium storing program code executable by one or more processors to implement:
  a. a user identification manager,
  b. a user profile manager,
  c. a user data access manager.

The method further includes providing a machine-readable storage encoded with non-transitory program code executable by one or more processors of a mobile communication device of a user to implement on the mobile device a user application to manage retrieval of personal information of the user stored in the one or more databases, the user application including:
  a. a user interface manager to manage a Graphical User Interface (GUI) to manage display of information to the user and manage user inputs through the GUI,
  b. a user authentication manager to manage user authentication and grant access to the user application when the user is successfully authenticated,
  c. a data exchange control manager to manage exchange of data between the mobile device and the server arrangement,
  d. the mobile communication device configured to communicate with the server arrangement, whereby:
    i. the user identification manager is responsive to credentials transmitted by the user application to identify a user profile associated with the user,
    ii. the user profile manager configured to generate a document index associated with the user profile, the document index identifying documents stored in the user record of the user, and transmit the document index to the user application,
    iii. the user interface manager being responsive to the document index to display via the GUI user-selectable input elements corresponding to respective documents in the user record, allowing the user to select via the GUI a document to be retrieved,
    iv. the user application configured to transmit to the user data access manager a user selection indicative of a document selected by the user to be retrieved,
    v. the user data access manager and the data exchange control manager configured to establish a stateless communication session including an encrypted communication channel and further configured to monitor transmission of the document selected by the user to be retrieved and when retrieval of the document by the mobile communication device is completed, disable the encrypted communication channel.

BRIEF DESCRIPTION OF THE DRAWINGS

A detailed description of embodiments of the invention is provided below, by way of example only, with reference to the accompanying drawings, in which.

It is to be expressly understood that the description and drawings are only for the purpose of illustrating certain embodiments of the invention and are an aid for understanding. They are not intended to be a definition of the limits of the invention.

DETAILED DESCRIPTION

Figure 1:
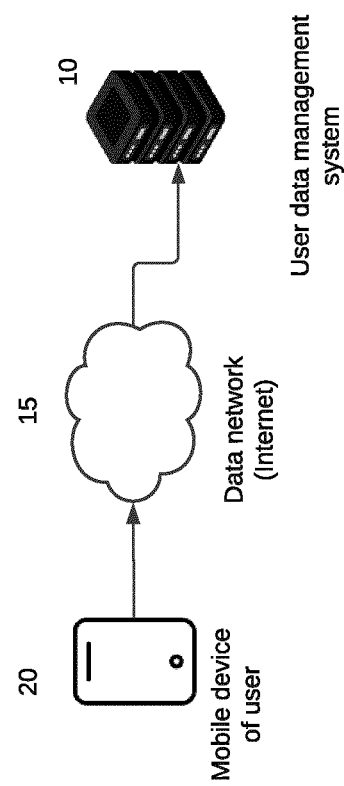
FIG. 1 is a block diagram of an electronic records system enabling users to access confidential user information via a data network (i.e., internet) via user devices such as mobile user devices.

FIG. 1 shows a block diagram of an electronic records system enabling users to access confidential information via a data network 15 (i.e., internet) with user devices such as mobile devices 20. The confidential information can include medical information such as medical records of the user, legal information, and financial information of the user such as banking information, among others.

The electronic records system shown in FIG. 1 has a user data management system 10 that includes data repository functions and data management functions. As it will be discussed in greater detail later, the user data is partitioned into individual blocks that are accessible one block at a time, such that the entire content of the user data record is never fully exposed. In this fashion, should an accidental data leakage occur, the exposure is limited to a single data block but not over the entire user record. Examples of blocks of confidential and/or privileged electronic data could be bank account #1, bank account #2, . . . , bank account #n, mortgage data, health record #1, health record #2, . . . , health record #n, etc.

In the embodiment shown in FIG. 1, the user data management system 10 resides at a single node of the data network. In this arrangement the user data is locally stored in a local database.

Figure 2:
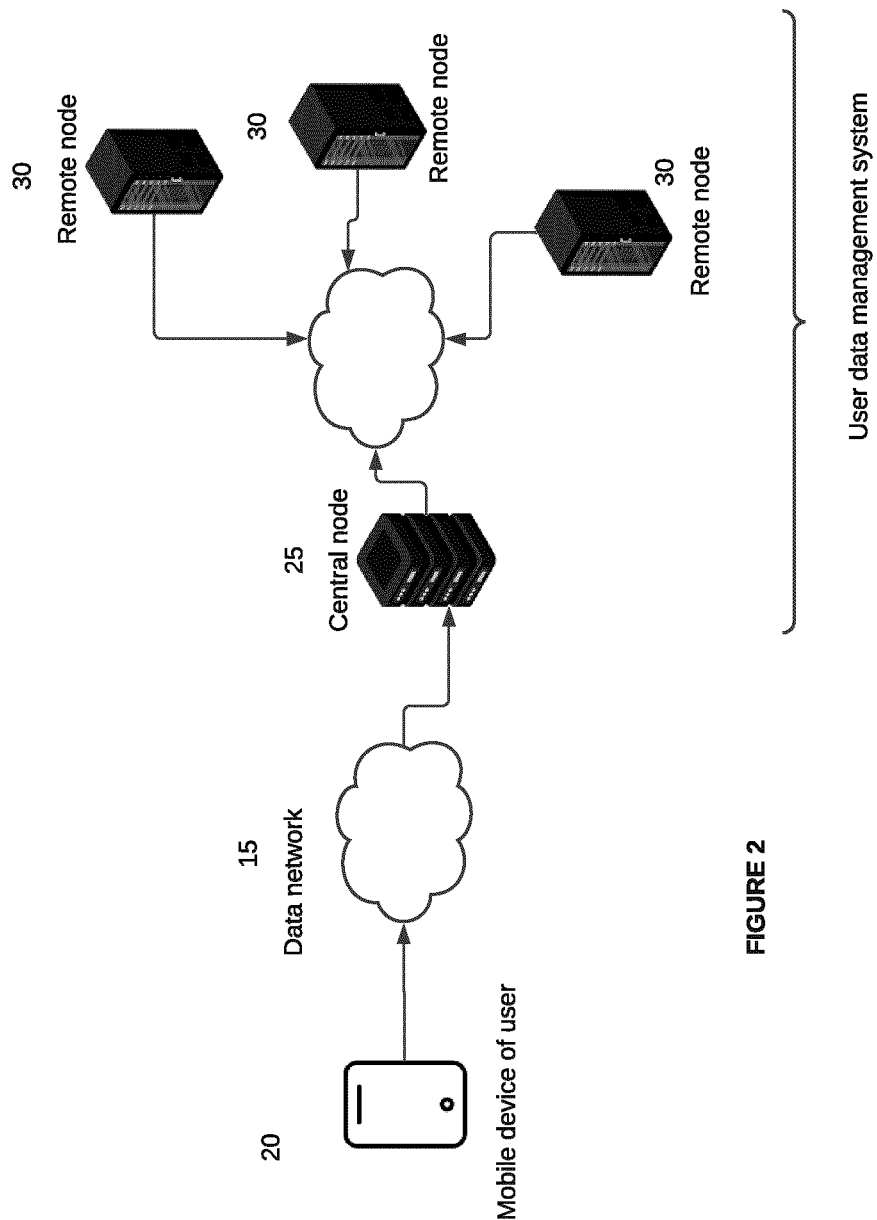
FIG. 2 shows a variant of the system shown in FIG. 1 where the user information is remotely distributed over several remote data storage nodes.

FIG. 2 is a variant of FIG. 1 wherein the confidential user information is remotely distributed across multiple databases, such as individual remote nodes 30 each holding a portion of the confidential information of the user. In this form of implementation, the remote nodes 30 together form the data repository, and a central node 25 stores an index of the data blocks making up the user records along with a list of pointers that point to the location of the actual data blocks at the respective remote nodes 30.

Figure 3:
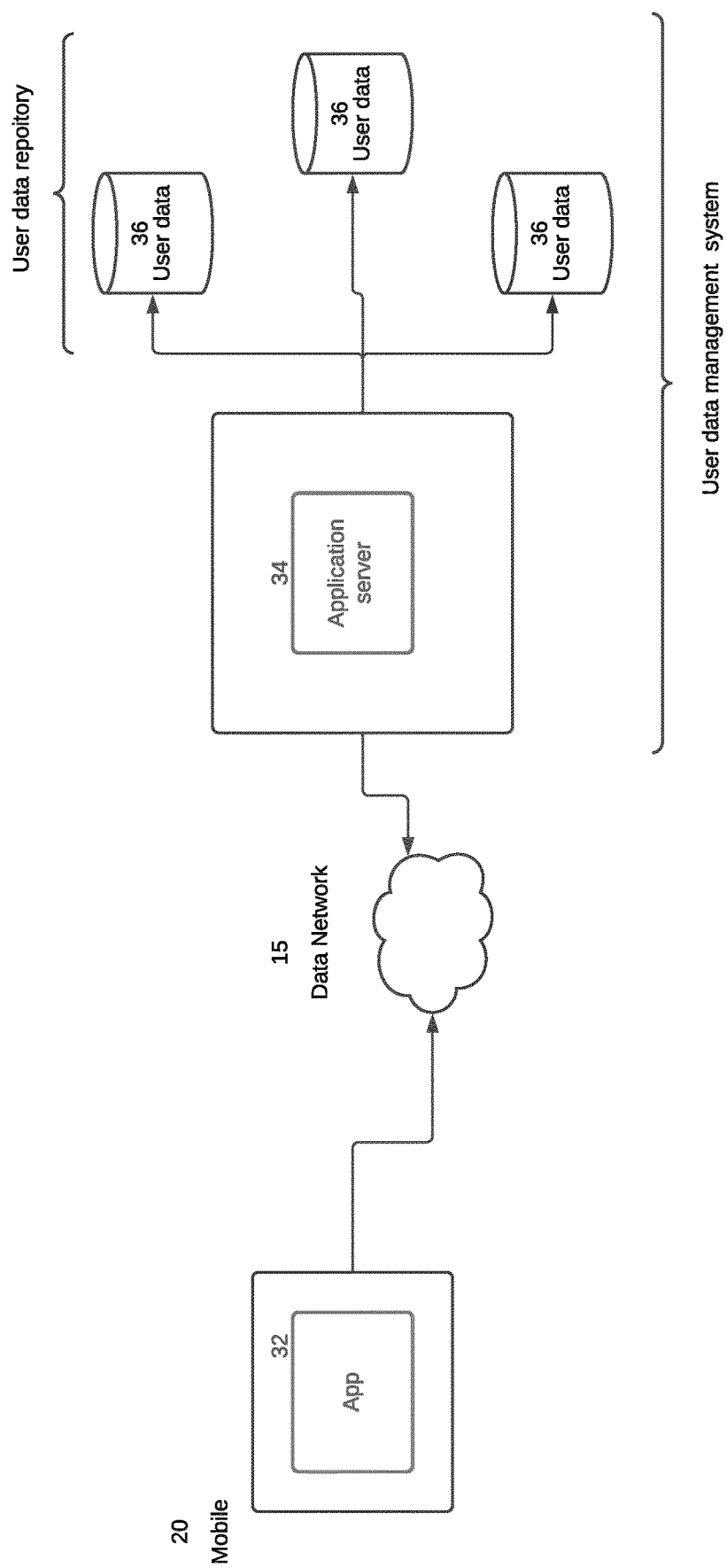
FIG. 3 is a block diagram illustrating software components used in the implementation of the system depicted in FIG. 1.

FIG. 3 is a high-level block diagram illustrating the main software components of the electronic records system shown in FIG. 1, both on the user device side and the user data management side which can be connected over data network 15.

In the context of a user device which is a mobile, the functionalities on the user side are implemented by an application ("app") 32 that is executed by the mobile device. The user data management system has an application server 34 that exchanges data with the app 32. The user data management system also includes the data repository including a one or more data bases 36 where the user data resides.

Secure user access to the confidential user information in the electronic records system shown in FIGS. 1 and 2 includes two important aspects. The first aspect is user identification, that is to say reliably associating a user that is interacting with the system with the proper user record maintained by the system. This is implemented by mapping the user device 20 to a user profile on the user data management side of the system 10. This can be performed by registering the user device 20 with the application server 34. The registration process maps the user device, in particular the app 32 to a user profile. In a specific example of implementation, the registration process involves generating at the application server-side a unique user identity code and transferring this code to the app 32, which is stored by the app 32. When the app 32 interacts with the application server 34, for instance to view a user document, the app 32 will send to the application server 34 the identity code, which constitutes credentials to a particular user profile. Accordingly, the application server 34 is capable to distinguish different users from each other on the basis of the respective identity codes that the respective apps 32 submit as credentials when they interact with the application server 34.

The second aspect of the secure user access is user authentication at the app side, which preferably is performed by the biometric user authentication services of the mobile device 20. User authentication ensures that the person who is granted access to the mobile device 20 and to the app 32 executed by the mobile device 20 is the rightful owner of the mobile device 20.

By combining such user authentication and user identification a secure data access is provided.

Figure 4:
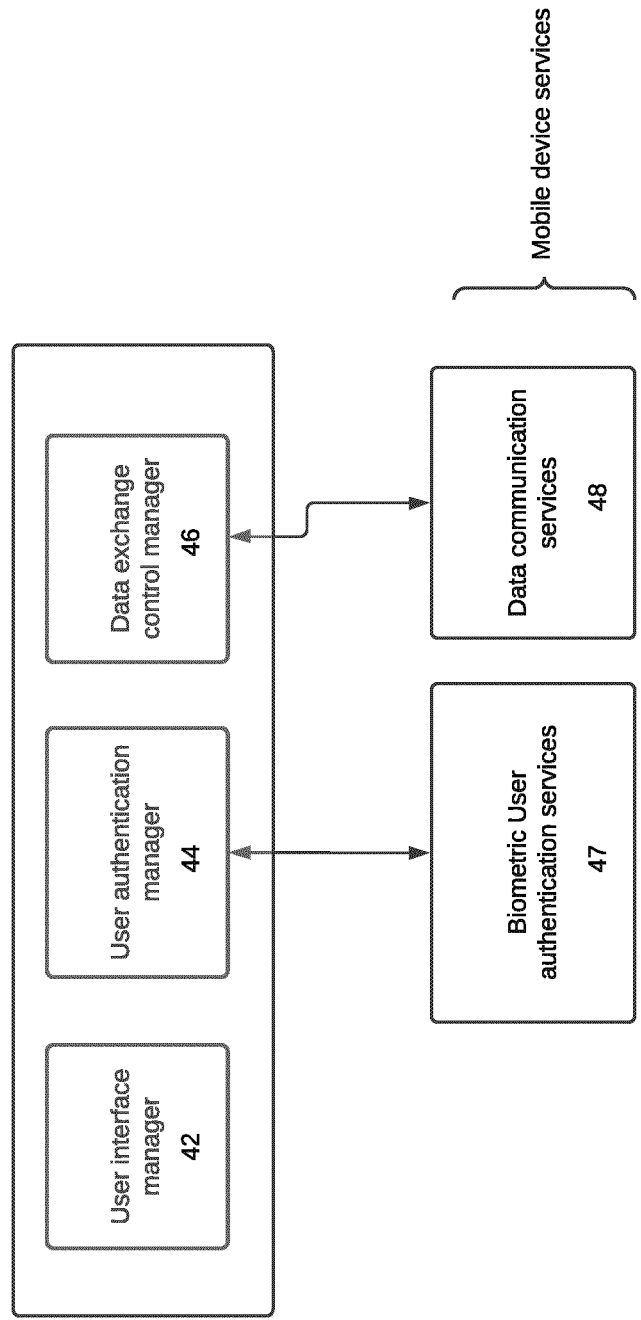
FIG. 4 is a more detailed block diagram of the software components implementing an app executed by a mobile device.

FIG. 4 is a more detailed block diagram of the mobile device app 32. The app 32 comprises three main modules: 1) a user interface manager 42, 2) user authentication manager 44 and 3) data exchange control manager 46, each of which will be described herein.

The user interface manager 42 is responsible for managing user interactions with the app 32 at the front end (i.e., displaying data, monitoring user inputs, etc.) via the user interface of the mobile, such as the touch sensitive screen of the mobile device 20.

The user authentication manager 44 is responsible for invoking the authentication services of the mobile device 20 when the app 32 is launched and before the user is allowed to use the app. The user authentication manager is in turn linked to the biometric user authentication services 47 of the mobile device. One example of biometric user authentication services is face recognition. Another example is fingerprint recognition. The data exchange control manager 46 is responsible for interacting with the data communication services 48 of the mobile to control the communication channel with the application server 34, in particular close the channel as a block of data requested by the user has been successfully uploaded.

Figure 5:
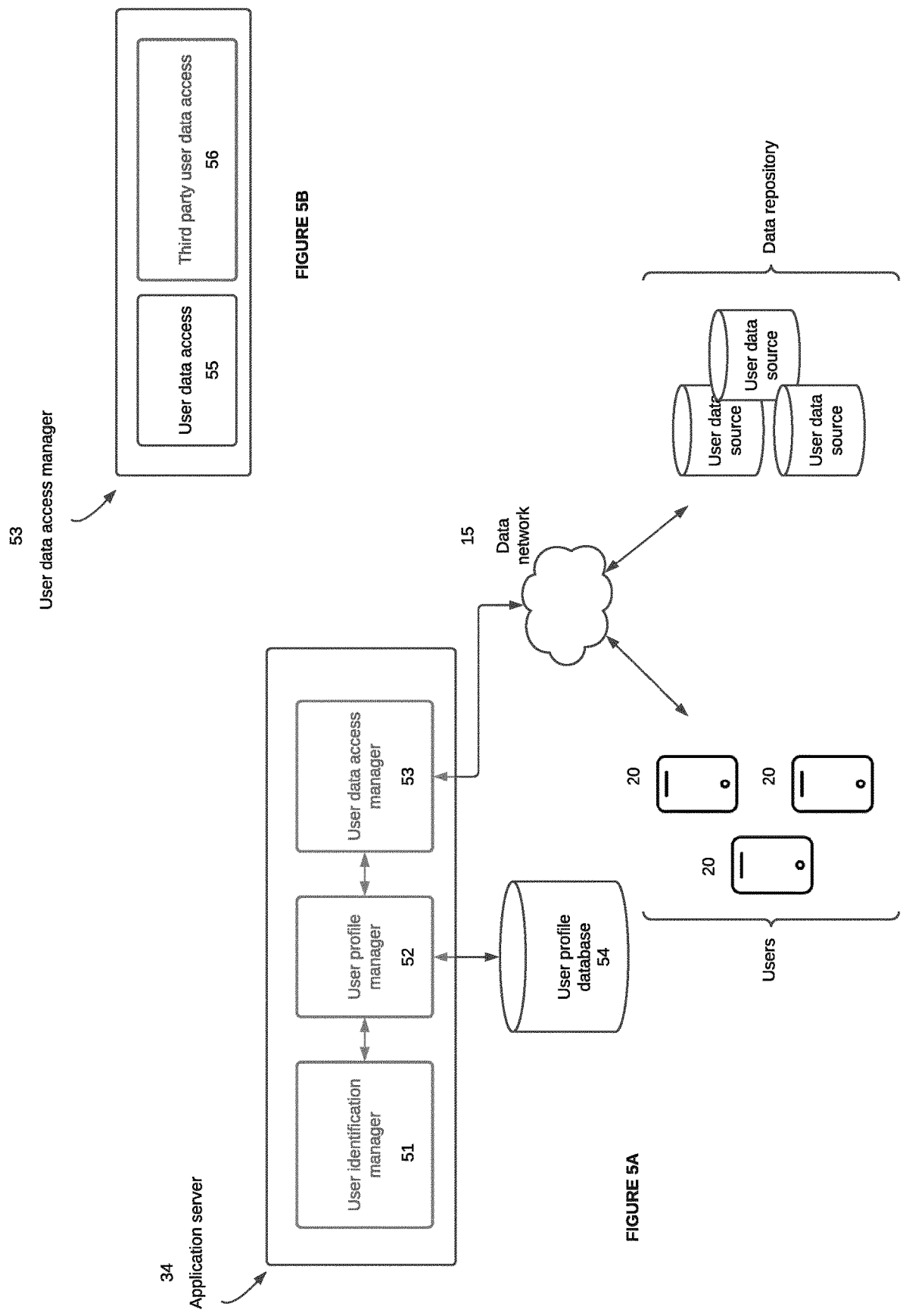
FIG. 5A is a block diagram of an application server at the back end of the system shown in FIG. 1.
FIG. 5B is more detailed block diagram of a user data access manager module shown in FIG. 5A.

FIG. 5A is a more detailed block diagram of the software modules of the application server 34. The application server 34 has a user identification manager 51 which performs user identification. The user identification manager 51 receives the identity code sent by a particular one of the mobile devices 20 interacting with the application server 34 and then maps that particular identity code to a particular user profile, it being understood that each identity code of the user base of the system is linked to a single user profile. In other words, the user identification manager 51 will determine the identity of the person associated with the mobile that has submitted the particular credentials (identity code) and retrieves the user profile associated with that identity.

The user profile manager 52 is responsible for operations involving information stored in the user profile. For instance, the user profile manager 52 will extract from a user profile database a document index associated with a particular user profile and then send this document index to the mobile device 20 such that the app 32 displays to the user the documents that are stored in the user record and that the user can chose to view on the screen.

The user data access manager 53 manages the transfer of the user data to the mobile 20 such that it can be viewed by the user. The data access manager 53 receives from the app 32 a user selection that identifies a particular document the user wants to see, will retrieve the selected document and transmit the document to the app 32, which will in turn display it to the user.

FIG. 5B provides a more detailed block diagram of the user data access manager. The user data access manager has two main functional blocks, one being the user data access function 55 which manages user access to data that belongs to the user. This function would typically be invoked when the user is authenticated and identified as discussed previously. The other functional block, which is the third-party user data access function 56 manages the access to user data by a third party. As discussed below, the user has the possibility to identify blocks of user information to share with a third party. The third-party user data access function 56 is responsible to allow a designated third party to access the selected information but block access to information that the user has not specifically designated for sharing.

Figure 6:
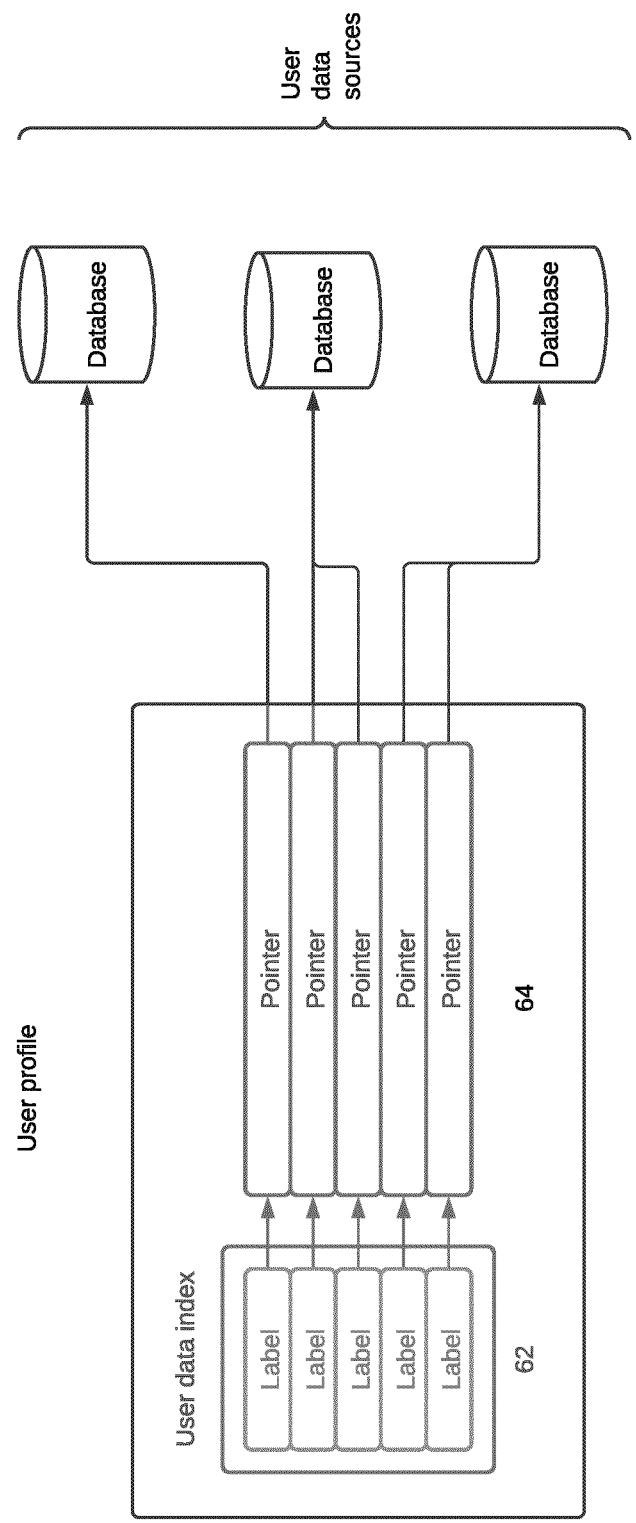
FIG. 6 is a block diagram of a data structure illustrating how user data is partitioned in individual blocks.

FIG. 6 is a block diagram illustrating how user data is structured and stored in the electronic records system. The user profile database stores a user data index which in a specific example can be a list of documents that are maintained for that particular user on the electronic records system. In a specific example, the documents can be of medical nature, such as blood test results, imaging results and drug prescriptions, among others. In another example, the documents can be of financial nature, such as bank account statements, there being one document for one bank account the user may have, another document for another bank account, etc. In yet another example, the documents may be legal documents, such as corporate documents, for example.

The data index comprises a list of labels 62, where each label is associated with a corresponding document. In this fashion, the list of labels 62 indicates to the user such that it has some meaning for the user. Each label is linked to a pointer 64 that designates the location where the data associated with that label is stored. As indicated previously, such data repository can be central in which case the documents are locally stored and the link is a local link. Alternatively, as illustrated in FIG. 2, the user data can be remotely stored in a number of different databases at respective network nodes. In this form of implementation, data associated with a particular user can be stored in a single remote node or stored at several remote nodes. As long as the pointer structure can uniquely identify the specific user data associated with a particular label, there is no need to provide at the remote nodes themselves any particular mechanism mapping the data blocks to respective user profiles.

Figure 7:
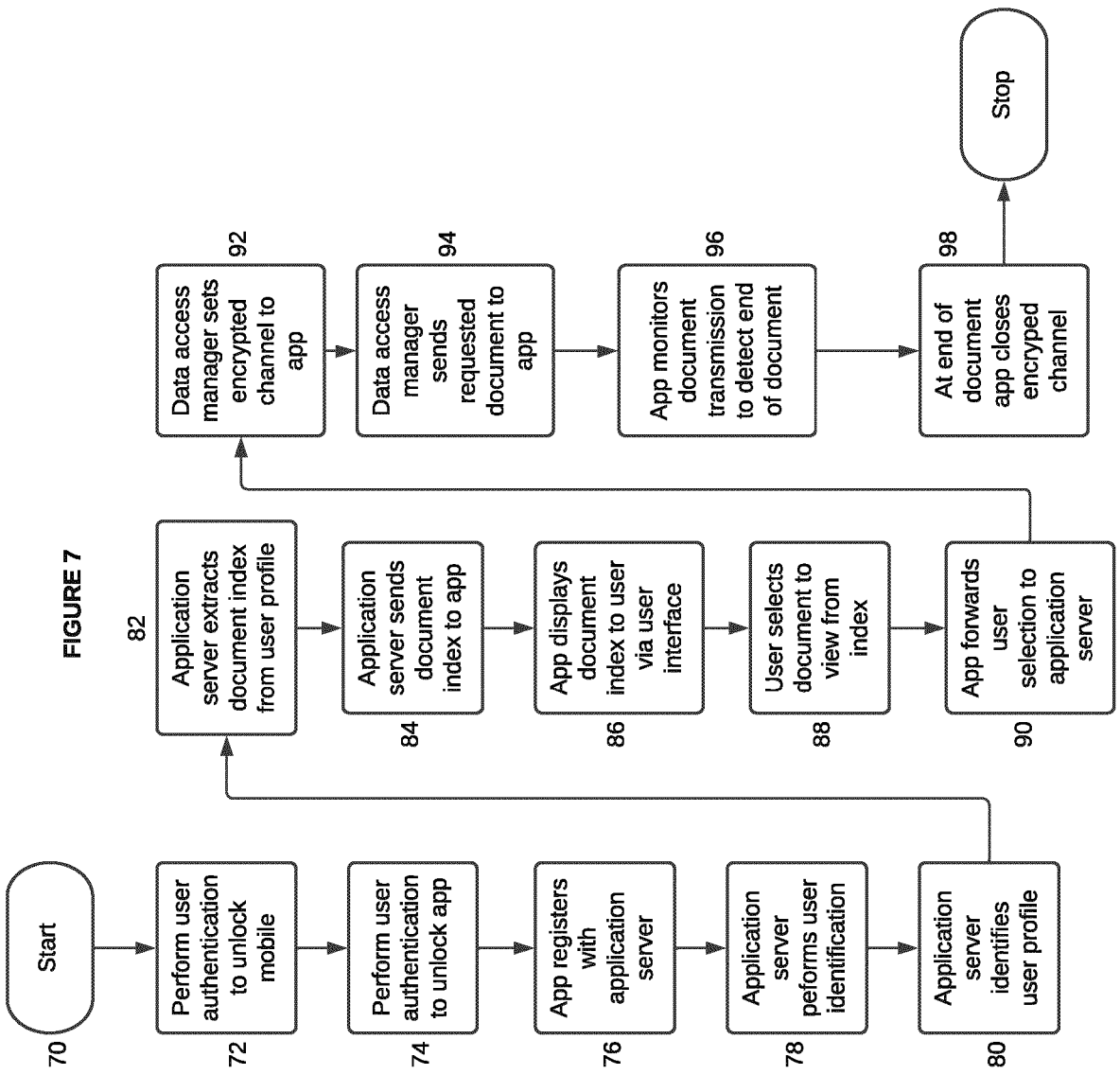
FIG. 7 is a flowchart of a multi-step process allowing a user to retrieve blocks of confidential data using his/her mobile device.

FIG. 7 is a flowchart illustrating the process performed by the electronic records system to retrieve and display a particular document that the user wants to see. The process starts at 70. At step 72, the user performs user authentication to unlock the mobile. This process uses the biometric user authentication of the mobile, such as face recognition or fingerprint recognition to unlock the mobile and allow the user to invoke the app 32. At step 74, the user performs user authentication at the app level. The app 32 will invoke the user authentication service of the mobile, namely the biometric user authentication, and if the authentication service validates the user, the app 32 will unlock and allow the user to interact with it.

At step 76, the app 32 will register with the application server to establish an interaction with the application server 34. During this step, the identity code stored by the app 32 is sent to the application server 34 as credentials. At step 78, the application server 34 will perform user identification by searching the user profiles for the one associated with the credentials submitted by the app 32. At step 80, the application server 34 locates the user profile associated with the submitted credentials. At step 82, the user profile manager module 52 of the application server extracts the user profile from the user profile database.

At step 84, the user profile manager module of the application server will send to the app the document index stored in the user profile such that it can be viewed by the user on the display of the mobile, as shown at step 86.

At step 88, the user selects a document to view from the index. At step 90, the app 32 forwards the document selection to the application server 34 and passes it to the user data access manager 53. The user data access manager 53 will then cross reference the user selection with the user profile to identify the pointer to the location that holds the data requested by the user. The user data access manager 53 will then retrieve the information from the location identified by the pointer, which can be a local location or a remote location.

At step 92, the data access manager 53 sets an encrypted communication channel over which the data so retrieved will be sent to the app 32. As part of the transmission, the user data access manager 53 will inform the app 32 of certain characteristics of the data block that is being sent, namely its size, such that the app 32 can monitor the progress of the transmission over the encrypted communication channel and detect the end of the transmission when all the data bytes have been safely received. At step 94, the user data access manager 53 initiates the transmission of the document over the encrypted communication channel.

At step 96 the app, in particular the data exchange control module 46 of the app 32, monitors the received data to detect the end of the transmission. Since the app was previously notified of the document size, the data exchange control module 46 counts the received bytes and can then determine when the last byte was received, which means the entire document has been safely received.

At step 98, the app 32 then closes the encrypted communication channel. When the channel is no longer maintained on the app side, the application server 34 drops the channel at its end.

If the user now wants to view another document, the entire process, starting at step 76 is repeated assuming the app 32 is still unlocked and accessible by the user. In this fashion, every data block sent by the application server 34, which would correspond to a single document, a document page or a group of pages, requires re-setting a new encrypted communication channel between the app 32 and the application server 34. Thus, data exposure over a communication channel is limited to a single block and should for some reason the communication channel become compromised, only one data block is compromised.

In a specific example of implementation, the communication process between the app 32 and the application server 34 is performed by using a stateless call process. In contrast to a more traditional state-based interaction between the app 32 and the application server 34, a stateless call is considered more secure because less information about the state of the interaction is stored on the application server side 34. To elaborate, in a state-based interaction, a session ID is generated to keep track of the session, especially when the app requests several web pages from the application server. A session ID is typically a short-live token as to maintain the interaction "live" between the app 32 and the application server 34. This makes it appear to the user at the mobile that the application server is in constant interaction with the app, while in reality it is not. The apparent continuity is made possible by using a session ID and storing the interaction state at each step.

It has been found advantageous from a data security perspective to use a stateless call instead of a session-based one, which requires storage of the interaction state to maintain session continuity. The stored data defining the interaction state contains sensitive information and maintaining this data, even on a short-term basis in the memory of the server attracts some element of data breach risk. Moreover, assuming a third-party gains access to a live session between the app and the application server, that access could extend to all the web pages exchanged during the session. For instance, assume that user wants to perform an online banking transaction. Once a session is established with the bank application server, the user can view all his/her bank accounts, which means that several web pages will be sent to the user, each associated with a different account, while the session is active. If a third party can tap into the data flow, that party will thus gain access to all the information sent over the link since it occurs in the context of a single session.

A stateless call is considered more secure since every time a new web page or more generally a document is requested by the app 32, the entire registration process, as shown at step 76 starts again. Note, step 78 may be performed in a way which is transparent to the user if the authentication performed previously has not timed out. When the document is delivered to the user, the mobile will close the call with the application server and no session state data needs to be stored. For any new web page requested, the process repeats. In this case, assuming a third-party gains access to the communication channel, that access will only extend to the data being transferred, which is single document or web page. For any new document, the third party will need to gain access to a newly establish communication channel, which is more difficult to accomplish.

Figure 8:
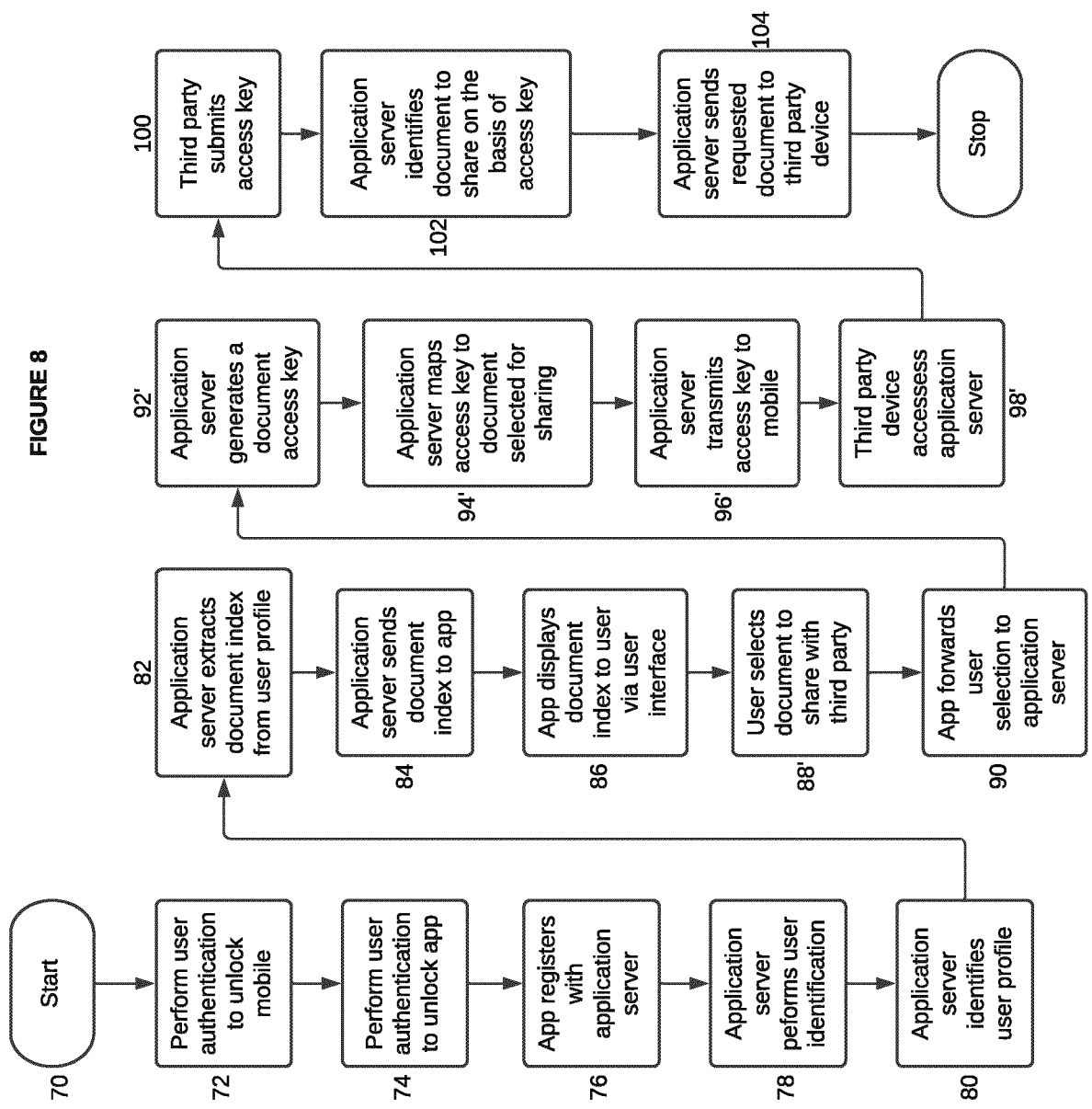
FIG. 8 is a flowchart of a multi-step process through which a user shares selected blocks of his/her confidential data with a third party while preventing the third party to access other blocks of the confidential data that the user does not want to share with the third party.

FIG. 8 is a flowchart of a process allowing a user to share confidential user data with a third party, under the control of the user, in other words the user is the one that selects the data that the third party will have access to and specifically, the data that the third party will not have access to. Steps 70 to 86 are identical to those shown and described in connection with FIG. 7 above.

Figure 9A:
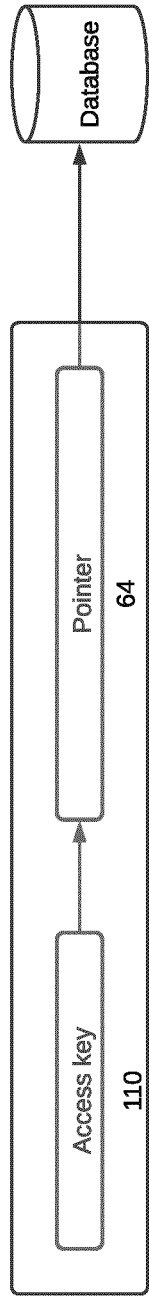
FIGS. 9A and 9B are non-limiting examples of a mapping between a third-party access key and the specific blocks of confidential data that the user wants to share with a third party.
Figure 9B:
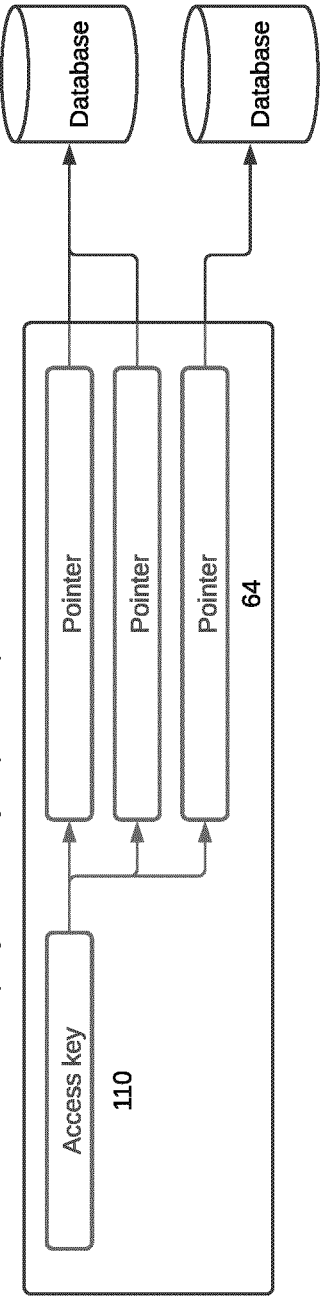

At step 88', the user selects a document in the index displayed on the mobile that the user wants to share with a third party. The user selection is forwarded by the app 32 to the application server 34 at step 90. At step 92', the third-party module of the user data access manager 53 generates an access key that the third party can use to gain access to the document selection. With specific reference to step 94' in FIG. 8 and FIGS. 9A and 9B, the third party will create a mapping between the access key 110, which can be any suitable identifier and the pointer 64 to the location where the document to be shared can be retrieved. FIG. 9A shows a scenario where a single document is to be shared, hence the access key 110 is linked to a single pointer, the one that corresponds to the selected document for sharing. In FIG. 9B, the user has selected several documents to share, and, in this instance, the third-party module of the user access manager 56 creates a mapping linking the access key 110 to several pointers, each one designating the location where the respective documents reside.

At step 96', the application server 34 sends the access key 110 to the app 32. In a specific example of implementation, the access key data sent to the app 32 includes the access key itself and a Uniform Resource Locator (URL) that the third party can invoke, supply the access key and access the user data. For instance, the URL access can be an address in the data network that can be accessed by a browser.

The access key data, including the access key and the URL can be displayed on the user mobile as a Quick Response (QR) code. In the situation where the third party is physically close to the user mobile and can scan the user mobile with a camera of the third-party device, as shown at step 98', the URL will be invoked and the access key suppled to the application server, as shown at step 100.

At step 102 the third-party module of the data access manager will receive the access key 110 and identify the mapping previously created at step 94' in order to retrieve the pointers to the documents to be shared, as shown at step 102. The documents to be shared are retrieved by using the pointers and they are sent to the third party at step 104.

Alternatively, the access key can be in the form of a pin that can be sent to the third party via email or text message, along with an URL, such as a browser address where the user documents can be viewed.

Note that while the third party can be a user device where a human will view the document that is being shared, the third party can be a computer-based agent that can process the received data based on logic rules to reach a certain conclusion.

The invention claimed is:

1. A system for secure communication of personal information, comprising:
 a. a server arrangement in communication with one or more databases storing personal information associated with multiple users, in respective user records, wherein the personal information is organized in each user records as a series of documents, the server arrangement including a non-transitory storage medium storing program code which, when executed by one or more processors, implements:
  i. a user identification manager,
  ii. a user profile manager,
  iii. a user data access manager,
 b. a non-transitory machine-readable storage medium encoded with program code, which, when executed by one or more processors of a mobile communication device of a user, implements on the mobile communication device a user application to manage retrieval of personal information from the one or more databases, the user application including:
  i. a user interface manager to control a Graphical User Interface (GUI) for managing display of information to the user and manage user inputs through the GUI,
  ii. a user authentication manager to manage user authentication and grant access to the user application when the user is successfully authenticated,
  iii. a data exchange control manager to manage exchange of data between the mobile communication device and the server arrangement,
 c. the mobile communication device configured to communicate with the server arrangement, whereby:
  i. the user identification manager is responsive to credentials transmitted by the user application to identify a user profile associated with the user,
  ii. the user profile manager configured to generate a document index associated with the user profile, the document index identifying documents stored in the user record of the user, and transmit the document index to the user application,
  iii. the user interface manager being responsive to the document index to display via the GUI user-selectable input elements corresponding to respective documents in the user record, allowing the user to select from the user-selectable input elements a document to be retrieved,
  iv. the user application configured to transmit to the user data access manager a user selection indicative of a document selected by the user to be retrieved,
  v. the user data access manager and the data exchange control manager configured to establish a stateless communication session including establishing an encrypted communication channel and further configured to monitor transmission of the document selected by the user to be retrieved and when retrieval of the document by the mobile communication device is completed, disable the encrypted communication channel.

2. The system as defined in claim 1, wherein the documents convey medical information of the user.

3. The system as defined in claim 1, wherein the documents convey financial information of the user.

4. The system as defined in claim 1, wherein the documents convey legal information of the user.

5. The system as defined in claim 1, wherein the user data access manager is configured to transmit to the user application data characterizing the document to be retrieved, the data exchange control manager configured to monitor data reception during document retrieval and detect on the basis of the data characterizing the document completion of the document retrieval and in response to detection of the completion of the document retrieval disable the encrypted communication channel.

6. The system as defined in claim 5, wherein the data characterizing the document conveys a size of the document.

7. The system as defined in claim 1, wherein the document to be retrieved is a first document, the user interface manager is responsive to a user input on the GUI displaying the user-selectable input elements indicative of a user request to retrieve a second document, wherein the user input is a second user input, in response to the second user input the user application re-transmitting to the user identification manager the credentials, allowing the user identification manager to re-identify the user profile.

8. The system as defined in claim 7, wherein in response to the re-identification of the user profile, the user profile manager is configured to re-generate the document index and transmit the re-generated document index to the user application.

9. A non-transitory machine-readable storage medium encoded with program code which, when executed by one or more processors of a mobile communication device of a user, implements on the mobile communication device a user application to manage retrieval of personal information of the user stored in one or more databases associated with a server arrangement, the user application including:
 a. a user authentication manager to manage user authentication and grant access to the user application when the user is successfully authenticated, in response to successful user-authentication initiate transmission of credentials to the server arrangement allowing the server arrangement to identify a user profile at the server arrangement associated with the user,
 b. a user interface manager to manage a Graphical User Interface (GUI) to manage display of information to the user and manage user inputs through the GUI, the user interface manager being responsive to a document index transmitted from the server arrangement to display on the GUI user-selectable input elements corresponding to respective documents in a user record maintained on the server arrangement and associated with the user profile, allowing the user to select via the GUI a document to be retrieved from the user record,
 c. a data exchange control manager configured to establish with the server arrangement a stateless communication session including establishing an encrypted communication channel and further configured to monitor transmission of a document from the user record corresponding to a user-selection at the GUI, via the encrypted channel, to detect a state of completion of the document transmission and in response to detection of the state of completion, disable the encrypted communication channel.

10. The non-transitory machine-readable storage medium as defined in claim 9, wherein the documents convey medical information of the user.

11. The non-transitory machine-readable storage medium as defined in claim 9, wherein the documents convey financial information of the user.

12. The non-transitory machine-readable storage medium as defined in claim 9, wherein the documents convey legal information of the user.

13. The non-transitory machine-readable storage medium as defined in claim 9, wherein the data exchange control manager is configured to detect the state of completion of the document transmission by monitoring a quantity of data received during the transmission.

14. The non-transitory machine-readable storage medium as defined in claim 13, wherein the data exchange control manager is configured to receive data conveying a size of the document before the document transmission is initiated.

15. The non-transitory machine-readable storage medium as defined in claim 9, wherein the document to be retrieved is a first document, the user interface manager is responsive to a user input on the GUI displaying the user-selectable input elements indicative of a user-request to retrieve a second document, wherein the user input is a second user input, in response to the second user input the user application re-transmitting to the server arrangement the credentials, allowing the server arrangement to re-identify the user profile.

16. A method for secure communication of personal information, comprising:
 a. providing a server arrangement in communication with one or more databases storing personal information associated with multiple users, in respective user records, wherein the personal information is organized in each user records as a series of documents, the server arrangement including a non-transitory storage medium storing program code which, when executed by one or more processors, implements:
  i. a user identification manager,
  ii. a user profile manager,
  iii. a user data access manager,
 b. providing a non-transitory machine-readable storage medium encoded with program code, which when executed by one or more processors of a mobile communication device of a user, implements on the mobile communication device a user application to manage retrieval of personal information of the user stored in the one or more databases, the user application including:
  i. a user interface manager to control a Graphical User Interface (GUI) for managing display of information to the user and manage user inputs through the GUI,
  ii. a user authentication manager to manage user authentication and grant access to the user application when the user is successfully authenticated,
  iii. a data exchange control manager to manage exchange of data between the mobile device and the server arrangement,
 c. the mobile communication device configured to communicate with the server arrangement, whereby:
  i. the user identification manager is responsive to credentials transmitted by the user application to identify a user profile associated with the user,
  ii. the user profile manager configured to generate a document index associated with the user profile, the document index identifying documents stored in the user record of the user, and transmit the document index to the user application,
  iii. the user interface manager being responsive to the document index to display via the GUI, user-selectable input elements corresponding to respective documents in the user record, allowing the user to select via the GUI a document to be retrieved,
  iv. the user application configured to transmit to the user data access manager a user selection indicative of a document selected by the user to be retrieved,
  v. the user data access manager and the data exchange control manager configured to establish a stateless communication session including establishing an encrypted communication channel and further configured to monitor transmission of the document selected by the user to be retrieved and when retrieval of the document by the mobile communication device is completed, disable the encrypted communication channel.

17. The method as defined in claim 16, wherein the documents convey medical information of the user.

18. The method as defined in claim 16, wherein the documents convey financial information of the user.

19. The method as defined in claim 16, wherein the documents convey legal information of the user.

20. The method as defined in claim 16, including transmitting to the user application data characterizing the document to be retrieved, the data exchange control manager configured to monitor data reception during document retrieval and detect on the basis of the data characterizing the document, completion of the document retrieval and in response to detection of the completion of the document retrieval disable the encrypted communication channel.

21. The method as defined in claim 20, wherein the data characterizing the document conveys a size of the document.

22. The method as defined in claim 16, wherein the document to be retrieved is a first document, the user interface manager is responsive to a user input on the GUI displaying the user-selectable input elements indicative of a user-request to retrieve a second document, wherein the user input is a second user input, in response to the second user input the user application re-transmitting to the user identification manager the credentials, allowing the user identification manager to re-identify the user profile.

23. The method as defined in claim 22, in response to the re-identification of the user profile, the user profile manager is configured to re-generate the document index and transmit the re-generated document index to the user application.

\* \* \* \* \*